United States Patent [19]

Chagnon

[11] Patent Number: 5,441,746

[45] Date of Patent: * Aug. 15, 1995

[54] ELECTROMAGNETIC WAVE ABSORBING, SURFACE MODIFIED MAGNETIC PARTICLES FOR USE IN MEDICAL APPLICATIONS, AND THEIR METHOD OF PRODUCTION

[75] Inventor: Mark S. Chagnon, Pelham, N.H.

[73] Assignee: Molecular BioQuest, Inc., Atkinson, N.H.

[*] Notice: The portion of the term of this patent subsequent to Feb. 14, 2002 has been disclaimed.

[21] Appl. No.: 57,687

[22] Filed: May 5, 1993

Related U.S. Application Data

[63] Continuation-in-part of Ser. No. 958,646, Oct. 7, 1992, Pat. No. 5,389,377, which is a continuation-in-part of Ser. No. 894,260, Jun. 8, 1992, which is a continuation-in-part of Ser. No. 566,169, Aug. 10, 1990, abandoned, which is a continuation-in-part of Ser. No. 455,071, Dec. 22, 1989, abandoned.

[51] Int. Cl.⁶ ............................................. A61K 9/127
[52] U.S. Cl. ........................................ 424/450; 424/490; 424/498; 424/600; 424/617; 424/630; 424/635; 424/639; 424/641; 424/644; 424/646; 424/650; 428/402.24
[58] Field of Search ............... 424/450, 490, 498, 600, 424/617, 630, 635, 639, 641, 644, 646, 650; 428/402.2

[56] References Cited

U.S. PATENT DOCUMENTS

| 4,106,488 | 8/1978 | Gordon | 128/1 R |
|---|---|---|---|
| 4,331,654 | 5/1982 | Morris | 424/38 |
| 4,426,330 | 1/1984 | Sears | 260/403 |
| 4,590,922 | 5/1986 | Gordon | 128/1.3 |
| 4,628,037 | 12/1986 | Chagnon et al. | 436/526 |
| 4,652,257 | 3/1987 | Chang | 604/52 |
| 4,675,173 | 6/1987 | Widder | |
| 4,690,130 | 9/1987 | Mirell | 128/1.3 |
| 4,945,049 | 7/1990 | Hamaya et al. | |
| 4,994,213 | 2/1991 | Aitcheson et al. | 264/4.6 |
| 5,013,556 | 5/1991 | Woodle et al. | 424/450 |
| 5,071,076 | 12/1991 | Chagnon et al. | |
| 5,091,187 | 2/1992 | Haynes | 424/450 |

FOREIGN PATENT DOCUMENTS

| 0125995 | 11/1984 | European Pat. Off. | G01N 33/54 |
|---|---|---|---|
| 0546939 | 6/1993 | European Pat. Off. | A61K 49/00 |
| 8911335 | 11/1989 | WIPO | B01J 13/02 |
| 9109678 | 7/1991 | WIPO | B03C 1/00 |

Primary Examiner—Gollamudi S. Kishore
Attorney, Agent, or Firm—Hayes, Soloway, Hennessey, Grossman & Hage

[57] ABSTRACT

This invention describes an electromagnetic wave-absorbing surface modified magnetic particle for use in medical applications. The magnetic particles are coated with an amphipathic organic compound and an amphipathic vesicle forming lipid. These particles may be used in a method of treatment of cancer, as well as for the treatment of infectious disease. For cancer treatment the invention comprises providing a patient said coated particles, absorbing the coated particle intracellularly into the cancer cell, and subjecting the patient to an alternating electromagnetic field to inductively heat the magnetic core particle along with the cancer cells. The inductive heating of the magnetic core particle is then continued so as to achieve an increase in intracellular temperature which selectively kills the cancer cells.

5 Claims, 1 Drawing Sheet

FIGURE 1

ELECTROMAGNETIC WAVE ABSORBING, SURFACE MODIFIED MAGNETIC PARTICLES FOR USE IN MEDICAL APPLICATIONS, AND THEIR METHOD OF PRODUCTION

This application is a continuation-in-part of U.S. application Ser. No. 07/958,646 filed Oct. 7, 1992, now U.S. Pat. 5,389,377 which is a continuation-in-part of U.S. application Ser. No. 07/894,260, filed Jun. 8, 1992, pending, which is a continuation-in-part of U.S. application Ser. No. 07/566,169, filed Aug. 10, 1990, now abandoned, which is a continuation-in-part of U.S. application Ser. No. 07/455,071, filed Dec. 22, 1989, now abandoned. Attention is also directed to commonly assigned, application Ser. No. 07/706,478, filed Dec. 13, 1991, and commonly assigned U.S. application Ser. No. 07/071,076, the disclosures of which are incorporated by reference.

FIELD OF THE INVENTION

This invention relates to a method of forming electromagnetic wave absorbing, surface modified magnetic particles for use in medical applications. Preferably, the particles have a uniform, controllable size, and a narrow size distribution, in the range of from about 1 to 50,000 nm in diameter. The particles of interest to this invention have a crystal structure that cause them to absorb electromagnetic wave energy and convert that energy to heat. The particles can be coated with organic moieties, such as lipids, therein forming a controlled size particle core liposome composition, which can pass freely through physiological membranes, while avoiding selected cell types. After passage through the membrane, the particle can be exposed to an electromagnetic field to thermally destroy cells or tissue local to the particle.

BACKGROUND OF THE INVENTION

An excellent review of some of the prior art methods for the treatment of cancer by the application of external electromagnetic energy, capable of generating heat in intracellular particles to induce selective thermal death of cancer cells, is provided for in U.S. Pat. No. 4,106,488 to Gordon. See also U.S. Pat. Nos. 4,590,922 and 4,690,130.

The Gordon patent reports that one common characteristic for all of the known techniques for treating cancer is that they are extracellular in scope, that is, the cancer cell is attacked and attempted to be killed through application of the killing force or medium outside of the cell.

Unfortunately, the extracellular approach has some longstanding and important limitations, not the least of which is the difficulty in penetrating the tough outer membrane of the cancer cell that is composed of two protein layers with a lipid layer in between. Of even greater significance is that to overcome the protection afforded the cell by the cell membrane in any extracellular technique, the attack on the cancer cells must be of such intensity that considerable damage is caused to the normal cells. This results in severe side effects upon the patient. These side effects have been found to limit considerably the effectiveness and usefulness of these treatments.

A safe and effective cancer treatment has been the goal of investigators for a substantial period of time. Such a technique, to be successful in the destruction of the cancer cells, must be selective in effect upon the cancer cells and produce no irreversible damage to the normal cells. In sum, cancer treatment must selectively differentiate cancer cells from normal cells and must selectively weaken or kill the cancer cells without affecting the normal cells.

It has been known that there are certain physical differences that exist between cancer cells and normal cells. One primary physical difference that exists is in the temperature differential characteristics between the cancer cells and the normal cells. Cancer cells, because of their higher rates of metabolism, have higher resting temperatures compared to normal cells. In the living cell, the normal temperature of the cancer cell is known to be 37.5° Centigrade, while that of the normal cell is 37° Centigrade. Another physical characteristic that differentiates the cancer cells from the normal cells is that cancer cells die at lower temperatures than do normal cells. The temperature at which a normal cell will be killed and become unable to perform normal cell functions is at a temperature of 46.5° Centigrade, on the average. The cancer cell, by contrast, will be killed at the lower temperature of 45.5° Centigrade. The temperature elevation increment necessary to cause death in the cancer cell is determined to be at least approximately 8.0° Centigrade, while the normal cell can withstand a temperature increase of at least 9.8° Centigrade.

It is known, therefore, that with a precisely controlled increment of heat, the cancer cells can be selectively destroyed before the death of the normal cells. On the basis of this known differential in temperature characteristics, a number of extracellular attempts have been made to treat cancer by heating the cancer cells in the body. This concept of treatment is referred to as hyperthermia. To achieve these higher temperatures in the cancer cells, researchers have attempted a number of methods including inducing high fevers, utilizing hot baths, diathermy, applying hot wax, and even the implantation of various heating devices in the area of the cancer.

At this time, none of the various approaches to treat cancer have been truly effective and all have the common characteristic of approaching the problem by treating the cancer cell extracellularly. The outer membrane of the cancer cell, being composed of lipids and proteins, is a poor thermal conductor, thus making it difficult for the application of heat by external means to penetrate into the interior of the cell where the intracellular temperature must be raised to effect the death of the cell. If, through the extracellular approaches of the prior hyperthermia techniques, the temperatures were raised so high as to effect an adequate intracellular temperature to kill the cancer cells, many of the normal cells adjacent the application of heat could very well be destroyed.

The Gordon patent, in an attempt to improve on the selectivity in killing cancer cells, disclosed a process wherein minute particles, capable of generation of heat upon application of electromagnetic energy, are injected intravenously, through the use of "suitable compatible liquid vehicles" which must sustain the particles in suspension for injection. Suitable vehicles are identified to include aqueous solutions of any body acceptable materials such as dextran, dextrose, saline or blood, as well as water alone. The minute particles suspended in the aqueous media are reported to be transported through the bloodstream and were found to be phagocytized by the cancerous cells to a far greater degree than, and in fact some cases to the possible exclusion of, their admittance into the normal cells.

With regards to improving on selectivity, liposomes and other lipid structures have been widely proposed for targeting of drugs to specific locations in the body. See, e.g. the discussion in parent and copending U.S. application Ser. No. 07/958,646, the teachings of which are incorporated by reference. There it is pointed out that liposomes are aqueous compartments enclosed by a lipid membrane bilayer. Such membrane structures allow liposomes to regulate the passage of an entrapped drug into the bloodstream, a feature that offers potential for improving drug effectiveness and reducing side effects associated with certain drugs. However, aqueous core liposomes have met with their own limited success owing, among other things, to the tendency of drug leakage from the liposomes prior to reaching the delivery site.

It was therefore recognized in U.S. application Ser. No. 07/958,646 that a need existed for a controlled size liposome therapeutic agent which was particulate in nature (i.e. a liposome with a uniform size inorganic particle core) which would improve on the problem of leakage from the liposome and offer additional advantages unique to a solid-core type construction. Accordingly, uniform size inorganic core liposomes were therein reported which demonstrated a much improved ability to specifically target and deliver drugs to tissue or organs over existing prior art methods. The liposomes of U.S. application No. 07/958,646 were also of unconventional design, comprising an inorganic core, an amphipathic organic compound, and an amphipathic vesicle forming lipid.

Accordingly, it is a general object of this invention to build upon the prior discovery reported in copending U.S. application Ser. No. 07/958,646 and develop a wave absorbing magnetic particle core liposome composition which substantially improves on selectivity and allows the particles to pass through specific physiological membranes, whereupon exposure to electromagnetic radiation, the selected cells or tissues are heated and destroyed.

A more specific object of this invention is to prepare uniform size wave absorbing magnetic particles that have a crystal structure that cause them to absorb electromagnetic wave energy and convert that energy to heat.

Still another objective of the invention is to provide a method of preparing a uniform size wave absorbing magnetic particle core liposome composition without requiring postliposome formation extrusion or other sizing procedures.

It is also an object of this invention to provide a wave absorbing magnetic particle core liposome coupled to novel phenyl lipids which additionally enhance the circulation time of the liposome in the bloodstream.

SUMMARY OF THE INVENTION

It has now been found that liposome compositions reported in copending U.S. application Ser. No. 07/958,646 can be prepared to comprise a wave absorbing magnetic core coated with an amphipathic organic compound and further coated with a second amphipathic vesicle forming lipid. In a preferred embodiment, the wave absorbing magnetic core particles comprise ferrite or mixed ferrite materials, preferably of a uniform, controllable size and narrow size distribution, wherein the primary component, the oxide, is of the formula $M_2(+3)M(+2)O_4$, wherein $M(+3)$ is Al, Cr or Fe, and $M(+2)$ is Fe, Ni, Co, Zn, Zr, Sr, Ca, Ba, Mg, Ga, Gd, Mn or Cd. In a further aspect, the oxides can be advantageously mixed with LiO, MaO and KO, or with $Fe_2O_3$ and $Fe_3O_4$.

The preparation of substantially uniform size oxides, 1 to 50,000 nm in diameter, is achieved by conversion of hydrous oxide gels, in a multi-step process, wherein alkali is added to individual $M(+3)$ and $M(+2)$ aqueous solutions, which separately precipitate the corresponding metal hydroxide. The two precipitates are then coarsely mixed to provide micron size amphorous gel particles, or the gels can be finally mixed by ball milling, for example, to a particle size of about 100 A in diameter. These particles are then heated to effect dehydration, in the presence of oxygen or air, wherein the dehydration temperature, time of dehydration, and concentration of oxygen or air operate to control the particle size of the oxide crystals therein produced.

In a further aspect, the invention includes a process for the treatment of cancer cells by application of external electromagnetic energy capable of the generation of heat in intracellular particles to induce selective thermal death of cancer cells comprising intravenously injecting into the patient a wave absorbing magnetic core particle coated with an amphipathic organic compound and further coated with a second amphipathic vesicle forming lipid, absorbing said coated wave absorbing magnetic core particle intracellulary into the cancer cells, subjecting the patient to an alternating electromagnetic field to inductively heat the magnetic core particle and thereby the cancer cells, and continuing the inductive heating of said magnetic core particle to attain an increase in intracellular temperature to selectively kill the cancer cells.

BRIEF DESCRIPTION OF THE DRAWINGS

Figure 1:
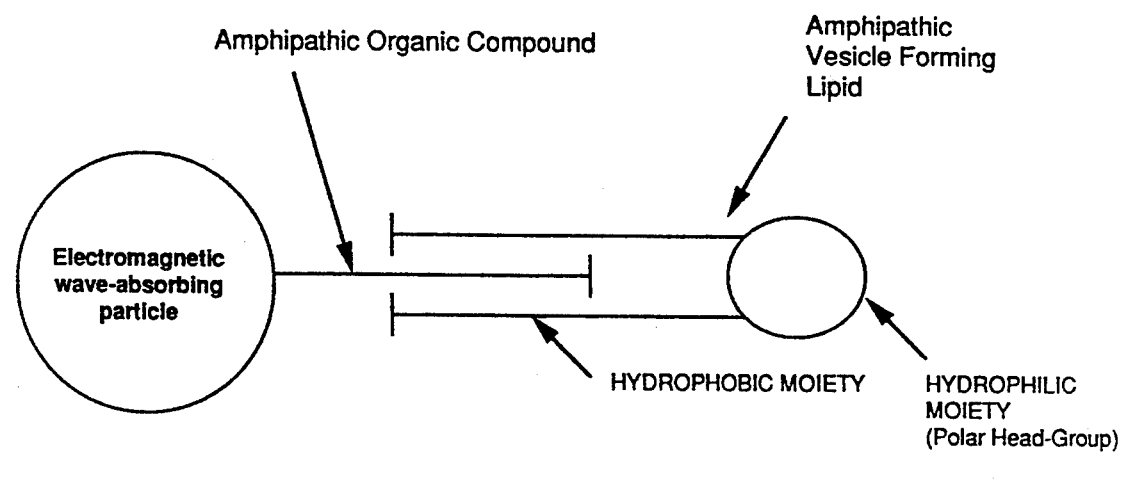

FIG. 1 illustrates the general liposome composition comprising a wave absorbing magnetic core particle coated with an amphipathic organic compound and further coated with an amphipathic vesicle forming lipid.

DETAILED DESCRIPTION OF THE INVENTION

I. Definitions

As used herein the term:

"Polyalkylether" refers to polyethyleneglycol and related homopolymers, such as polymethylethyleneglycol, polyhydroxypropyleneglycol, polypropyleneglycol, polymethylpropyleneglycol, and polyhydroxypropyleneoxide, and to heteropolymers of small alkoxy monomers, such as polyethylene/polypropyleneglycol, such polymers having a molecular weight of at least about 120 daltons, and up to about 20,000 daltons.

"Amphipathic organic compound" refers to any organic compound containing both a hydrophobic and hydrophilic moiety.

"Amphipathic vesicle forming lipid" refers to any lipid having a hydrophobic unit and hydrophilic unit, the hydrophobic group typically including two acyl hydrocarbon chains, the hydrophilic group containing a reactive chemical group such as amine, acid, ester, aidehyde, or alcohol group by which the lipid can be derivatized, e.g. to a polyalkylether.

II. Preparation of Wave Absorbing Magnetic Core Particles

The wave absorbing magnetic core particles suitable in the present invention are those particles which, upon application of an electromagnetic field, create inductive heat local to the particle. In a preferred embodiment, the wave absorbing magnetic core particles comprise ferrite or mixed ferrite materials, preferably of a uniform, controllable size, and narrow size distribution, wherein the primary component, the oxide, is of the formula $M_2(+3)M(+2)O_4$, wherein $M(+3)$ is Al, Cr or Fe, and $M(+2)$ is Fe, Ni, Co, Zn, Ze, Ca, Ba, Mg, Ga, Gd, Mn or Cd. In a further aspect, the oxides can be advantageously mixed with LiO, NaO and KO, or with $\alpha$ or $\gamma$ $Fe_2O_3$ and $Fe_3O_4$.

The preparation of substantially uniform size oxides, 1 to 50,000 nm in diameter, is achieved by conversion of hydrous oxide gels, in a multi-step process, wherein alkali is added to individual $M(+3)$ and $M(+2)$ aqueous solutions, which separately precipitate the corresponding metal hydroxide. The two precipitates are then coarsely mixed to provide micron size amorphorus gel particles, which can be milled to form hydrous oxide gel particles about 100 A in diameter. These particles are then heated to effect dehydration, in the presence of oxygen or air, wherein the dehydration temperature, time of dehydration, and concentration of oxygen or air operate to control the particle size of the oxide crystals therein produced.

For example, in connection with the above, a dehydration temperature of 100° C., at a time of about 6 hours, in the presence of oxygen, provides oxides particles of about 70A diameter. Alternatively, a dehydration temperature of about 65° C., at a time of about 24–36 hours, in the presence of oxygen, affords oxide particle sizes of about 1000–2000A. Accordingly, by recognizing that short dwell times and high temperature promote small oxide particle formation, and that long dwell times and low temperature promote large particle formation, oxide particles from 50A to several microns in diameter have been produced.

Heretofore, the use of ferrite materials as a protective medium for electromagnetic radiation reflecting surfaces was well known. In the present invention, however, it has been found that very small ferrospinal particles provide a high degree of absorbtion of electromagnetic waves. It has also been found that the complex permeability of certain ferromagnetic metallic oxides varies with frequency in such a way as to provide high absorption of electromagnetic magnetic radiation over wide frequency ranges without using large amounts of absorber material. Upon exposure to electromagnetic waves, these ferrites generate significant infra-red radiation over short distances local to the ferrite particle's surface.

In general, those ferrites suitable for use in the present invention are cubic crystalline materials characterized by a spinal structure containing $Fe_2O_3$ and at least one other oxide, usually of a bivalent metal, e.g. lithium oxide, cadmium oxide, nickel oxide, iron oxide and zinc oxide.

The ferrite materials of this invention can also be prepared by a thermal process, in which they are mixed together then ground together mixed and fired at about 1200° C. in a tube furnace for four hours or made by oxidation of ferrite powders from metal hydroxide gels. The imaginery permeability must be high enough to produce a large loss. For high frequencies, it has been found that nickel can replace lithium and for narrow bands zinc can replace cadnium.

One preferred mixed ferrite having the composition 0.45 LiO, 0.5 $Fe_2O_3$+0.30 $CdFe_2O_4$+0.25 $Fe_3O_4$ yielded the following results:

| Frequency Range (mHz) | % Absorbance | Surface Temp |
| --- | --- | --- |
| 1800–2500 | 98 | 230 |

As noted above, ferrites of interest to this invention can also be prepared by conversion of hydrous oxide gels in a multistep process. In one particular preferred example, alkali is added to a ferrous sulphate solution at a temperature between 15° and 40° C., in a stoichiometric amount adapted to precipitate ferrous hydroxide, from the Fe++ ion. At the conclusion of said precipitation, air is blown into the slurry, thus oxidizing ferrous hydroxide to goethite, FeO(OH).

During a second step, alkali is added to the slurry obtained in the first step. The remaining Fe++ is precipitated in the form of ferrous hydroxide, and the slurry is heated to a temperature between 70° C. and 100° C. thus causing the formation of ferrite which is then separated from the solution.

Accordingly, the present invention provides a process suitable for treating ferrous sulphate solutions in order to obtain ferrite exhibiting an equiaxial morphology with a narrow particle size distribution.

III. Amphipathic Organic Compounds

The amphipathic organic compounds which can be used in forming a liposome composition comprising the wave absorbing magnetic core particle may be selected from a variety of organic compounds which contain both a hydrophobic and hydrophilic moiety. According to one important aspect of the invention, it has been discovered that the hydrophilic moiety is adsorbed or coordinated onto the surface of the wave adsorbing magnetic core particle, whereas the hydrophobic moiety of the molecule extends outwardly to associate with amphipathic vesicle forming lipid compounds.

When the wave absorbing magnetic core particle is freshly made $Fe_3O_4$, it has been found, as reported in copending parent application 07/894,260, filed Jun. 8, 1992, that surface trivalent elements of the core particle contain imperfections which makes them available for direct covalent attachment with organometallic compounds of the formula $Ti(OR)_4$, wherein R is an alkyl group. Accordingly, the wave absorbing magnetic core particle can be coated with an organometallic coating covalently bonded to said particle wherein the bonding does not depend upon hydroxy functionality on the surface of said particle. Such coated particles can then be associated with an amphipathic vesicle forming lipid.

Preferred amphipathic organic compounds include fatty acids selected from the group consisting of oleic, stearic, linoleic, linolenic, palmitic, myristic and arachidonic acid.

IV. Amphipathic Vesicle Forming Lipid

The lipid components used in forming the wave absorbing magnetic core particle liposomes of the invention may be selected from a variety of vesicle forming lipids, typically including phospholipids, such as phosphatidylcholine (PC), phosphatidic (PA), phosphatidylinositol (P1), sphinogomyelin (SM), and the glycolipids, such as cerebroside and gangliosides. The selection of lipids is guided by consideration of liposome toxicity and biodistribution and targeting properties. A variety of lipids having selected chain compositions are commercially available or may be obtained by standard lipid isolation procedures. See, e.g. U.S. Pat. No. 4,994,213.

The lipids may be either fluidic lipids, e.g. phospholipids whose acyl chains are relatively unsaturated, or more rigidifying membrane lipids, such as highly saturated phospholipids. Accordingly, the vesicle forming lipids may also be selected to achieve a selected degree of fluidity or rigidity to control the stability of the liposome in serum. See, e.g. U.S. Pat. No. 5,013,556.

In a preferred embodiment, the vesicle forming lipid include those phospholipids in which the polar-head-group region is modified by the covalent attachment of polyalkylene ether polymers of various molecular weights. The attachment of the relatively hydrophilic polyalkylene ether polymer, particularly polyethylene oxide, alters the hydrophilic to hydrophobic balance within the phospholipid in order to give unique solubility to the phospholipid compound in an aqueous environment. See, e.g. U.S. Pat. No. 4,426,330. The polyalkyl ether lipid is preferably employed in the wave absorbing magnetic core particle liposome composition in an amount between about 1–20 mole percent, on the basis of moles of derivatized lipid as a percentage of total moles of vesicle-forming lipids. The polyalkylether moiety of the lipid preferably has a molecular weight between about 120–20,000 daltons, and more preferably between about 1000–5000 daltons.

In yet another embodiment of the present invention, phenyl lipid compounds (as reported in copending U.S. application Ser. No. 07/958,646) can be employed as amphipathic vesicle forming lipid components. These phenyl lipids have the structural formula:

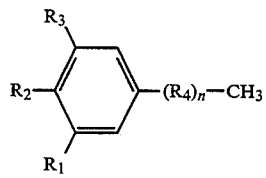

wherein two of $R_1$, $R_2$ and $R_3$ represent a saturated or unsaturated straight-chain or branched chain hydrocarbon group, the other being hydrogen, therein providing at least two hydrocarbon chains attached to the phenyl moiety, wherein the two hydrocarbon chains are typically between about 14–22 carbon atoms in length, and have varying degrees of unsaturation. $R_4$ represents the repeating unit of either a poly(alkylene oxide) polymer, preferably ethylene, propylene and mixtures thereof, or the repeating unit of poly(vinyl alcohol), or a polycarbohydrate. The number of alkylene oxide or vinyl alcohol groups in the polymer, designated as n, may vary from 0 to about 200 or more.

V. Preparing the Wave Absorbing Magnetic Core Particle Liposome Composition

One preferred method for producing the wave absorbing magnetic core liposome composition begins with first coating the magnetic particles described above in Section II with an amphipathic organic compound which contains both a hydrophillic and hydrophobic moiety. For example, fatty acids, such as oleic acid, linoleic acid or linolenic acid, dispersed in an organic solvent, are directly added to the particles at a ratio of dry ferrite:acid equal to 2:1 weight percent. After mechanically milling the mixture for 1 to 1.5 hours on a ball mill with 4 mm glass media, the acid coated particles collapse around the media allowing for easy removal of water without the loss of the particles. The coated particles are then dispersed in an organic solvent by addition of 700 ml of hexane, toluene or chloroform and mechanically milling with glass media overnight (15 hrs).

Absorbing a phospholipid onto the fatty acid coated particles was accomplished by addition of a synthetic polyethylene glycol terminated phosphatidyl ethanolamine to the above dispersion and mechanically mixing for 3 hours. The ratio of fatty acid:pure lipid is about 1:1 weight percent.

To transfer the particles from an organic phase to an aqueous phase, 7 mls of the dispersion was placed into a 14 ml glass vial with 3 ml of distilled water. The vial was placed in warm, 35° C. sonicating water bath with $N_2$ bubbling through it to evaporate the solvent. Once the solvent has evaporated, the aqueous dispersion was then suspended in a total of 10 mls of autoclaved water, sonicated for one hour, and centrifuged for 5 minutes. The supernatant was removed and brought to 20 mg particle/ml solution with autoclaved water.

6. Utility

The targeted wave absorbing magnetic core liposome may be prepared to include ferrites useful as cancer chemotherapeutic agents. In one method of synthesis, the magnetic core liposomes are prepared to include PEG-PE and PG on the liposome backbone to aid in targeting to specific areas and to avoid RES uptake.

Magnetic liposome compositions are also useful for radio-imaging or MRI imaging of solid tumor regions prior to EM wave exposure and cell destruction. The magnetic liposomes are prepared with encapsulated radio-opaque or particle-emission metal oxides or ferrites which substantially prevents permeation through the magnetic liposome bilayer.

In still another application, the magnetic liposome composition is designed to enhance uptake of circulating cells or other blood-borne particles, such as bacteria, virus-infected blood cells and the like. Here the long-life magnetic liposomes are prepared to include surface-bound ligand molecules, as above, which bind specifically and with high affinity to the selected blood-borne cells. Once bound to the blood-borne particles, the magnetic liposomes can be exposed to EM fields for specific cell or virus destruction.

Other objects and advantages of this invention will become apparent upon consideration of the following working examples.

EXAMPLE 1

Preparation of Absorbing Ferrite by Thermal Processes

A mixture consisting of nickel oxide (NiO), zinc oxide (ZnO), ferric oxide ($Fe_2O_3$) was mixed in a muller for 1 hour. The resulting powder was then screened through a 20 mesh screen. The powder was then treated in an oven at 350 degrees C. for 48 hours. The powder was then sintered at 1260 degrees C. in contact with air for 24 hours, and then cooled to room temperature over a period of 24 hours. Powders of different compositions were manufactured by varying the ratio of nickel oxide and zinc oxide in accordance with the relationship NiOxZnO-Fe$_2$O$_4$ where x is varied between 0.3 and 1.0. Frequency range absorbances are specified for some of the compositions in the following table.

TABLE 1

| COMPOSITION | (X) | FREQUENCY RANGE (mHz) | % ABSORBANCE |
|---|---|---|---|
| NiOZnOFe$_2$O$_4$ | .3 | 55–105 | 89 |
| NiOZnOFe$_3$O$_4$ | .6 | 145–1040 | 66 |
| NiOZnOFe$_2$O$_4$ | .9 | 530–2750 | 105 |

EXAMPLE 2

Preparation of Ferrite by Hydroxide Gel Process 0.148 moles of FeCl$_3$ was dissolved in 50 ml distilled water then precipitated with 150 ml of 1M NaOH. 0.037 moles of FeCl$_{12\cdot 4H2O}$ was dissolved in 50 ml distilled water then precipitated with 25 ml of 1M NaOH. 0.0185Moles CaCl$_2$ was dissolved in 50 ml distilled water and precipitated with 25 ml of 1M NaOH. 0.0185 moles ZnCl$_2$ was dissolved in 50 ml distilled water and precipitated with 25 ml of 1M NaOH. All four precipitated solutions were added together in a large beaker and mixed vigorously for four min. in an industrial blender. The resulting gel was heated at 90 degrees C. for 6 hours. O$_2$ was bubbled through the solution for the entire 6 hours.

EXAMPLE 3

Preparation of Ferrite by Hydroxide Gel Process 0.148 moles of FeCl$_3$ was dissolved in 50 ml distilled water then precipitated with 150 ml of 1M NaOH. 0.037 moles of FeCl$_{12\cdot 4H2O}$ was dissolved in 50 ml distilled water then precipitated with 25 ml of 1M NaOH. 0.037 Moles MnCl$_2$ was dissolved in 50 ml distilled water and precipitated with 25 ml of 1M NaOH. All three precipitated solutions were added together in a large beaker and mixed vigorously in a blender for four min. The resulting gel was heated at 90 degrees C. for 6 hours. O$_2$ was bubbled through the solution for the entire 6 hours.

EXAMPLE 4

Preparation of Ferrite by Hydroxide Gel Process 0.148 moles of FeCl$_3$ was dissolved in 50 ml distilled water then precipitated with 100 ml of 0.1M LiOH. 0.037 moles of FeCl$_{2\cdot 4H2O}$ was dissolved in 50 ml distilled water then precipitated with 25 ml 0.1MLiOH. Both precipitated solutions were added together in a large beaker and mixed vigorously for four min. The resulting gel was heated at 90 degrees C for 6 hours. O$_2$ was bubbled through the solution for the entire 6 hours.

EXAMPLE 5

Preparation of Ferrites from Hydroxide Gels

A reactor provided with a heat exchange coil and a radial stirrer, was fed with 3600 ml of ferrous sulphate solution having a concentration of 40 g/liter. Subsequently, 290 ml of ammonia solution (200 g/liter of NH$_3$) were added thereto, while stirring at 100 rpm. Such stirring was carried on throughout the first step. Air was blown into the reactor at a flow rate of 100 cc/hr. and the temperature was kept at about 30 Deg. C by cooling the heat exchange coil with water. The first step of the reaction was concluded when the pH value decreased to 3.5 and the platinum electrode, with respect to the calomel electrode, indicated +110mV. This occurred about 7 hours after the beginning of the flowing in of air.

The analysis of the slurry was as follows:
Fe++, 11.1 g/liter; Fe=37.1 g/liter.

160 ml of a ferrous sulphate solution (63.5 g/liter of Fe++) were admixed with the slurry. After this adjustment, the analysis of the slurry was as follows:
Fe++=13.1 g/liter; Fe=38.5 g/liter, the FeII/FeIII ratio being 0.52.

The reactor was fed with 155 ml of an ammonia solution (195 g/liter of NH$_3$) with stirring at 110 rpm. This stirring was continual throughout the second step. The temperature was brought to 90 degrees C. by conveying steam into the heat exchange coil, and the temperature was kept constant by means of a thermostat. During the reaction the pH value decreased from 8 to about 6.5. The second step of the reaction was terminated when the redox potential rose from −700 to about −450 mV. This occurred about 3 hours from the beginning of the heating. At the end, the ferrous iron present as Fe(OH)$_2$ was 0.34 g//liter of FeII. The slurry was acidified to a pH value −4 to remove ferrous hydroxide. The magnetic particles, once filtered, washed and dried, exhibited the following characteristics:

| | |
|---|---|
| Morphology | Cubic |
| Average Diameter d10 | 0.182 |
| Numerical variancy Coefficient | 22.0% |
| Mg content | 0.04% |
| S content | 0.61% |
| Specific surface magnetization 5680 G/domain | 6.52 m$^2$/g |

EXAMPLE 6

Preparation of Oleic Acid Coated Magnetic Particles

Wave absorbing magnetic particles, coated with oleic acid were prepared using the ferrites prepared in Examples 1–5.

The ferrite powder is dispersed in a beaker with approximately 1500 cc distilled water, adjusted to a concentration of approximately 10 wt % and stirred with a paddle stirrer for about 5 minutes. The beaker containing the ferrite slurry is then placed onto a permanent magnet, separating the wave absorbing magnetic particle from the aqueous salt waste solution. After resting the slurry on the magnet for 5 minutes, the aqueous salt solution is decanted. The precipitate is then resuspended by agitation in an additional 1500 cc of fresh distilled water. After the final water wash is decanted, the particles are suspended in acetone and the above washing procedure is repeated 5 times. The particles are then washed with hexane a total of five times each in the above manner.

Oleic acid is added to the magnetic particle/hexane slurry in a ratio of 2:1 oleic acid:dry particle. The mixture is adjusted to 15% total solids with hexane and milled overnight on a mechanical jar roller in a glass jar half filled with 3 mm stainless steel balls.

The samples were labeled 1–5 to correspond to the ferrites prepared in Examples 1–5.

EXAMPLE 7

Preparation of Phenyl Lipid

A. Synthesis of a m-isophthalic acid based phenyl lipid.

The starting material for this synthesis if 5-Aminoisophthalic acid. The 5-aminoisophthalic acid is not soluble in dioxane alone. It is soluble in a mixture of dioxane and triethylene glycol. 5-aminoisophthalic acid (145 mg) was dissolved in 5 ml. of dioxane and 2 ml. of triethylene glycol, and the pH was adjusted to 10 with NaOH. Methoxypolyoxyethylene imidazoly carbonyl, average mol. wt. 5,000 from Sigma (2.0g) was dissolved in 2 ml of $H_2O$, 1.0 ml of 1N $Na_2CO_3$, and 2.0 ml of triethylene glycol. This solution was added to the 5-aminoisophthalic acid solution and stirred for 36 hours at room temperature. The reaction mixture was then dialyzed overnight against 2 liters of $H_2O$. The dialyzed reaction mixture was mixed with 100 ml of pyridine and the liquids removed via rotary evaporation. The resulting yellow oil was placed in the refrigerator. After several days a white precipitate formed. The precipitate contains both coupled and uncoupled PEG.

Oleyl alcohol can be coupled to the above isophthalic acid derivative using thionyl chloride. The thionyl chloride can be used to activate the oleyl alcohol for ester formation with the carboxyl groups of the isophthalate. See. FIG. 2.

B. Synthesis of ortho phenyl lipids

The ortho analog of the phenyl lipids can be synthesized starting with either 3,4 dihydroybenzaldehyde or 3,4 dihydroxybenzoic acid. The aldehyde group can be coupled to an amino group by forming the Schiff's base and then reducing it with $NaBH_4$. Oleic acid could then be coupled to the hydroxyl groups using thionyl chloride to provide:

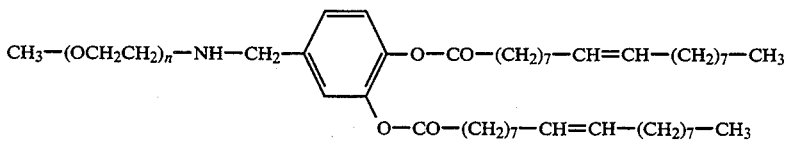

3,4 dihydroxybenzolic acid could be coupled through its carboxyl group to amino-terminated PEG using dicyclohexyl carbodiimide. Oleic acid could then be coupled as above.

Since both amino and carboxyl PEG derivatives as well as both oleic acid and oleylamine are available, the PEG and oleic acid groups can be easily interchanged in the above compounds.

EXAMPLE 8

Preparation of Magnetic Liposomes Using Phosphatidyl Choline 10 grams of each of the oleic acid coated ferrite as prepared in Example 6 were dispersed in 100 cc hexane. The phospholipid was absorbed onto the particle by dissolving phosphatidyl choline (Sigma, P-3644, L-2 lecithin, 45% PC) into hexane with heating to create a 15% solution. The PC/hexane solution was combined with the magnetic particles/hexane solution at a ratio of pure phosphatidyl choline:oleic acid equal to 1:2 weight percent.

The solution was mixed in a glass jar (without media) on a jar roller for two hours. 50 cc of distilled water were added to the jar and mixing was continued for an additional 1 hour. The jar and its contents were then transferred to an ultrasonic bath and treated by ultrasound for an additional 30-60 minutes.

The slurry was transferred to a 200 cc beaker and heated on a hot plate to 100 dcg C. for 10 min. From 0.05 to 50 grams of triton x-114 (Union Carbide) was added to disperse the lipidized ferrite in water. A ratio of triton X114:lipid particle equal to 1:6 weight percent was the optimum level for the dispersion. The dispersion was mixed on a laboratory vortex mixer for 2 minutes and placed in an ultrasonic bath (Branson 1200, VWR) for two hours. The final dispersion was adjusted to 0.2% TS (2 mg/ml). Particles were measured on a Nycomp laser particle size analyzer and were found to be approximately 200 nm in diameter.

EXAMPLE 9

Preparation of Magnetic Liposomes using Phenyl Lipid

Samples were prepared using particles from Examples 1-5 exactly as described in Example 8 except that phenyl lipids prepared in Example #7 was used in place of PC.

Samples were labeled for later i.d. 6-10 to correspond with the particles as prepared in Examples 1-5. Samples were measured for particle size on a nycomp particle analyzer and found to be approximately 200 nm in diameter.

EXAMPLE 10

Preparation of MDCK Cell Cultures

Upon the arrival, ampules of CCL34, MDCK cells (NBL-2 canine kidney) from ATCC, are quickly thawed. Using a sterile Pasteur pipette the contents of the ampule are transferred to a flask containing at least 10 volumes of culture medium (Eagles MEM) previously adjusted to pH 7.4. The cells are incubated for 24 hours, the media is withdrawn, discarded and replaced. Cells are incubated at 36.5 degrees C. in a $CO_2$ incubator for approximately 7 days. Another medium change may be necessary if indicated by a drop in pH or high cell concentration.

Cells are transferred during log phase, once confluence has been reached. The procedure is as follows: The media is withdrawn and discarded. A PBSA (5 ml/25cm 2) prewash is added to the flask opposite the cell monolayer. To avoid disruption the cells are rinsed and the solution discarded. Next, 3 ml/25 cm 2 trypsin is added to the flask (opposite of cells). The flask is turned to expose the cells to the trypsin for 15-30 seconds, then the trypsin is discarded making sure the monolayer is not detached. The cells are incubated until the monolayer will slide down the flask surface when tipped. (Approximately 5-15 min.) MEM medium is used to disperse the cells by repeated pipetting. Cells are diluted to 10-100 cells/ml and seeded in transwells as follows: Costar 6 well transwell-COL(3418) with pore size of 3.0 micron and well and 1.5 ml of culture (media and cells) are added to the inside of the transwell. The wells are covered and incubated until the monolayer is established on the membrane. The cell cultures thus prepared were used for all further experiments.

EXAMPLE 11

Ferrites were prepared as described in Examples 1-5, coated with oleic acid as in Example #6 and treated with a second layer of phenyl lipid as described in Example #7.

A culture of MDCK cells were prepared as described in Example #10. The lipid coated ferrites and uncoated (bare) ferrite controls were put in contact with the MDCK cells grown above a colony of rat brain cancer cells (neuroblastoma).

The sample was allowed to incubate at room temperature for a period of 1 hour, then exposed to a frequency of 20000 mHz for 3 minutes. None of the bare ferrite were permeable to the endothelial cell (MDCK) membrane and had no effect on the cancer cell colony.

Ferrites as prepared in Example 1, 2, 3 and 4 rapidly heated upon exposure to the EM wave and all the brain cells in the culture were killed.

Ferrites as prepared in Sample #5 were able to cross the endothelial cell barrier, however, because they are all iron, do not absorb EM waves and had no effect on the neuroblastoma cells.

I claim:

1. A composition comprising a wave absorbing magnetic core particle wherein said magnetic core particle comprises an oxide of the formula $M_2(+3)M(+2)O_4$ wherein $M(+3)$ is Al, Cr or Fe, $M(+2)$ is Fe, Ni, Co, Zn, Ca, Ba, Mg, Ga, Gd, Mn or Cd, in combination with an oxide selected from the group consisting of LiO, CdO, NiO, FeO, ZnO, NaO, KO and mixtures thereof, characterized in that said core is capable of adsorbing or coordinating with a hydrophilic moiety, coating with a first amphipathic organic compound, characterized in that said first amphipathic organic compound contains a hydrophilic moiety and a hydrophobic moiety and the hydrophilic moiety is adsorbed or coordinated with the core and the hydrophobic moiety thereby extends outwardly from the inorganic core and further coated with a second amphipathic organic compound wherein said second amphipathic compound contains hydrophobic and hydrophilic moiety and the hydropholic moiety associates with the outwardly extending hydrophobic moiety of said first amphipathic compound to form said wave absorbing composition.

2. The composition of claim 1, wherein the wave absorbing magnetic core particle has a diameter of less than 100 nm.

3. The composition of claim 1 wherein the amphipathic organic compound is a fatty acid selected from the group consisting of oleic, linoleic, linolenic, palmitic, myristic and arachidonic acid.

4. The composition of claim 1 wherein said second amphipathic organic compound is selected from the group consisting of phospholipids, sterol lipids and glycolipids.

5. The composition of claim 4 wherein the phospholipid is selected from the group consisting of phosphatidylcholine, phosphatidic acid, phosphatidylinositol, and phosphatidal ethonalamine.

* * * * *

UNITED STATES PATENT AND TRADEMARK OFFICE
CERTIFICATE OF CORRECTION

PATENT NO. : 5,441,746
DATED : August 15, 1995
INVENTOR(S) : Mark S. Chagnon

It is certified that error appears in the above-indentified patent and that said Letters Patent is hereby corrected as shown below:

Claim 1, Col. 14, line 14, "hydropholic" should be --hydrophobic--.

Signed and Sealed this

Ninth Day of April, 1996

Attest:

BRUCE LEHMAN

Attesting Officer

Commissioner of Patents and Trademarks